United States Patent [19]

Hood et al.

[11] Patent Number: 5,330,481
[45] Date of Patent: * Jul. 19, 1994

[54] APPARATUS FOR IMPLANTATION AND EXTRACTION OF OSTEAL PROSTHESES

[75] Inventors: Larry L. Hood, Laguna Hills; Robert C. Klapper, Los Angeles; James T. Caillouette, Newport Beach; Alexander Ureche, Mission Viejo, all of Calif.

[73] Assignee: Advanced Osseous Technologies, Inc., Aliso Viejo, Calif.

[ * ] Notice: The portion of the term of this patent subsequent to Feb. 8, 2011 has been disclaimed.

[21] Appl. No.: 838,879

[22] Filed: Feb. 18, 1992

Related U.S. Application Data

[60] Continuation-in-part of Ser. No. 706,786, May 29, 1991, which is a division of Ser. No. 475,492, Feb. 6, 1990, Pat. No. 5,045,054, and Ser. No. 704,467, May 23, 1991, which is a continuation of Ser. No. 304,820, Jan. 31, 1989, Pat. No. 5,019,083.

[51] Int. Cl.[5] .............................................. A61B 17/00
[52] U.S. Cl. .......................................... 606/99; 606/86; 604/22; 623/23; 128/898
[58] Field of Search ............. 606/53, 86, 90, 99, 606/171; 604/22; 128/898; 623/23, 22, 18, 16

[56] References Cited

U.S. PATENT DOCUMENTS

| | | |
|---|---|---|
| 3,862,630 | 1/1975 | Balamuth . |
| 3,990,452 | 11/1976 | Murry et al. . |
| 4,184,510 | 1/1980 | Murry et al. . |
| 4,222,382 | 9/1980 | Antonsson et al. ............... 623/23 |
| 4,248,232 | 2/1981 | Engelbrecht et al. . |
| 4,634,419 | 1/1987 | Kreizman et al. ................ 604/22 |
| 4,642,121 | 2/1987 | Keller ............................... 606/99 |
| 4,686,971 | 8/1987 | Harris et al. ...................... 606/99 |
| 4,705,038 | 11/1987 | Sjostrom et al. . |
| 4,705,500 | 11/1987 | Reimels et al. . |
| 4,750,488 | 6/1988 | Wuchinich et al. . |
| 4,768,496 | 9/1988 | Kreizman et al. . |
| 4,783,656 | 11/1988 | Katz et al. . |
| 4,974,581 | 12/1990 | Wiksell ............................. 604/22 |
| 5,080,685 | 1/1992 | Bolesky et al. .................. 623/23 |

FOREIGN PATENT DOCUMENTS 8802250 4/1988 PCT Int'l Appl. .

Primary Examiner—Stephen C. Pellegrino
Assistant Examiner—Jeffrey A. Schmidt
Attorney, Agent, or Firm—Knobbe, Martens, Olson & Bear

[57] ABSTRACT

Disclosed are improved methods and apparatus for implantation and extraction of osteal prostheses. Ultrasonic energy coupling adapters are disclosed for propagating ultrasonic energy along an incidence axis which deviates from a longitudinal axis of the prosthesis within a predetermined angular range. Methods of implantation and extraction of osteal prostheses are also disclosed, in which ultrasonic energy is propagated along an axis which extends at an angle with respect to a longitudinal axis of the prosthesis.

23 Claims, 7 Drawing Sheets

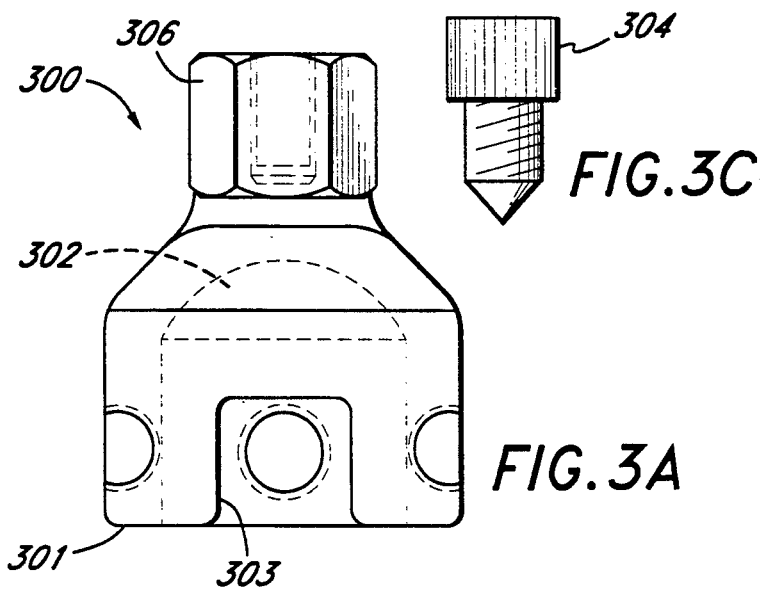
FIG. 3C
FIG. 3A
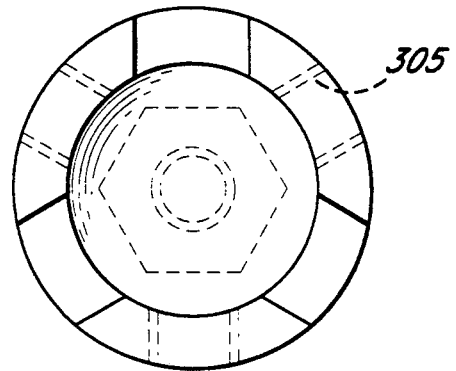
FIG. 3B
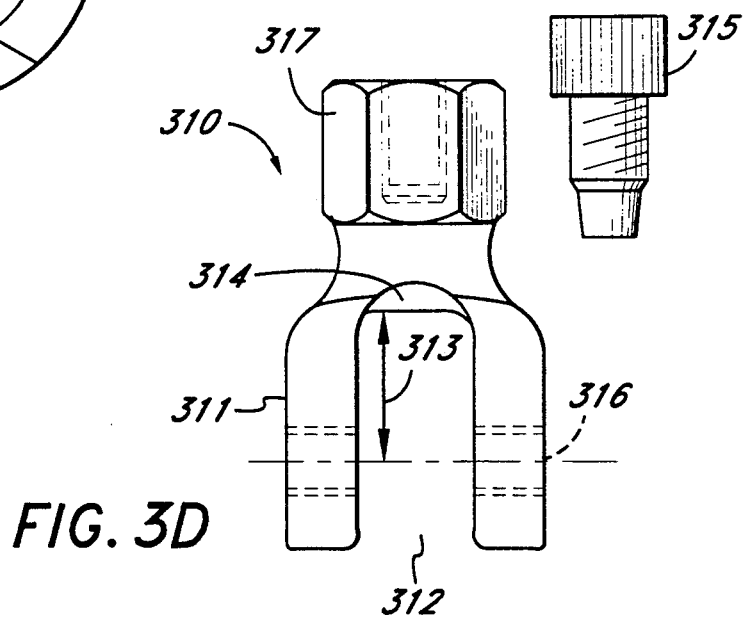
FIG. 3F
FIG. 3D
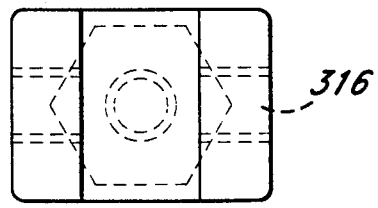
FIG. 3E

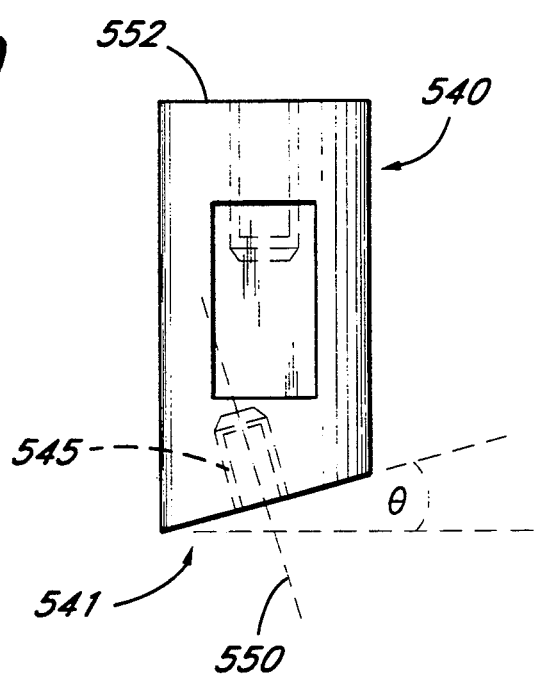
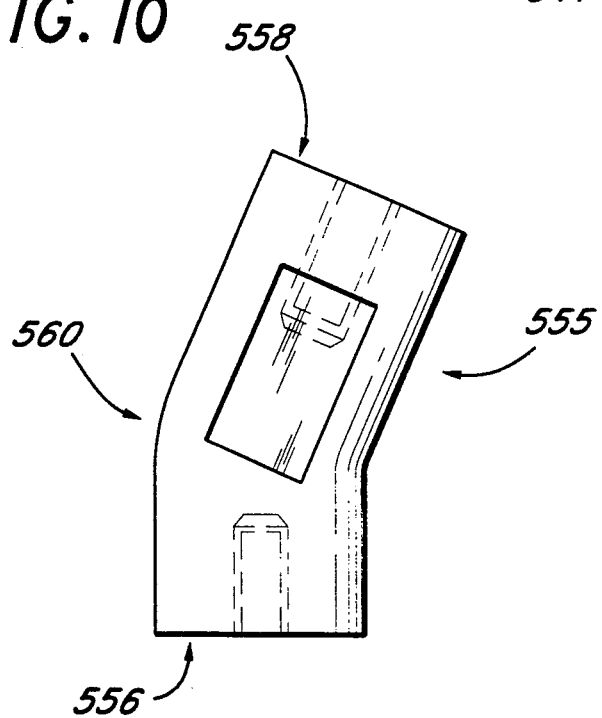
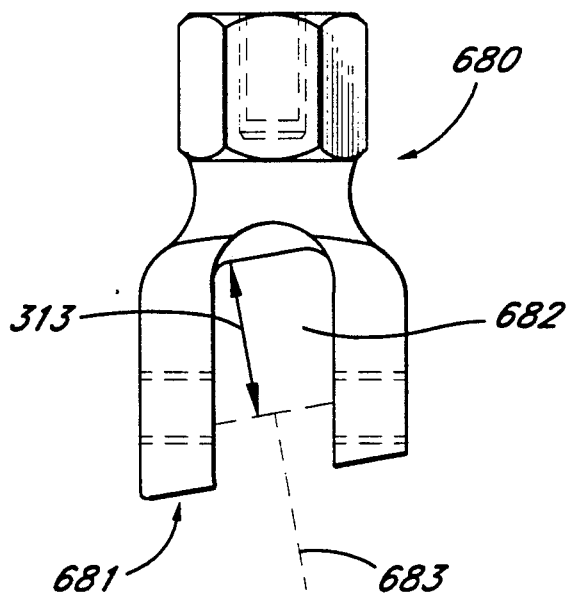

APPARATUS FOR IMPLANTATION AND EXTRACTION OF OSTEAL PROSTHESES

This is a continuation-in-part of co-pending application Ser. No. 07/706 786, filed May 29, 1991 which in turn is a divisional of application Ser. No. 07/475,492, filed Feb. 6, 1990, which issued as U.S. Pat. No. 5,045,054 on Sep. 3, 1991; and of application Ser. No. 704,467, filed May 23, 1991, which is a continuation of application Ser. No. 304,820 filed Jan. 31, 1989, which issued as U.S. Pat. No. 5,019,083.

BACKGROUND OF THE INVENTION

This application relates to an apparatus for the implantation and extraction of osteal prostheses employing an ultrasonic energy source and designed for use by orthopedic surgeons.

A variety of techniques and apparatus for implanting and removing orthopedic prostheses have been developed since replacement parts of hip joints and like were first used well over half a century ago. In particular, total joint replacements have been carried out in a large number of patients for some time. While some improvements have been made both in the techniques for implanting the prosthetic devices and in the prostheses themselves, a need remains for improved surgical procedures which are less time consuming and minimize trauma to the patient.

Revision total hip arthroplasty for replacement of defective or damaged prostheses has in particular taken on increasing importance, as the number of patients requiring such revisions increases dramatically. The procedures currently employed often result in complications, many of which are related to removal of the femoral prosthesis and the intramedullary cement mantle. The increased operating time required for revisions is associated with increased blood loss, a higher infection rate and increased postoperative morbidity. Femoral perforation during cement removal, with the possibility of intraoperative or postoperative femoral fracture, is a well-known and particularly serious complication.

None of the previously available procedures for removal of the femoral prosthesis and cement mantle is entirely satisfactory. For example, while high speed cutting tools (such as the Midas Rex and Anspach pneumatic tools) have been found effective in cement removal, the use thereof may be hazardous due to the fact that the femoral cortex is easily perforated. Image intensification may reduce the risk of perforation somewhat, but is time-consuming and adds the additional risk of excessive radiation exposure. The alternative technique of controlled femoral perforation requires wide soft tissue exposure and creates multiple potential stress risers; as it has been argued that any cortical defect (including such deliberately induced perforations) could increase the chances of intraoperative or postoperative fracture, such procedure is clearly not without a potentially significant risk of serious injury to the patient.

In an effort to provide improved procedures for the removal of the femoral cement mantle, various new techniques have been developed. For example, a $CO_2$ laser has been employed for cement removal. In this context, use of a laser has been found to have some significant disadvantages. The instrumentation required is cumbersome; moreover, vaporization of the cement is slow, the fumes toxic and flammable, and the potential for thermal necrosis of endosteal bone significant. Similarly, the lithiotriptor was explored as a potential tool for fracturing the cement mantle. It was determined, however, that the shock wave is difficult to focus, and thus microfractures of adjacent cortical bone occur frequently.

Systems using ultrasonic generators in conjunction with transducer or horn elements have heretofore been developed for use in specific medical applications. A variety of ultrasonic tools are currently employed almost routinely by practitioners in a number of fields, including neurosurgery, ophthalmology and dentistry. As these devices are tailored for use in particular surgical applications, they are found to have little if any applicability outside the particular context for which they were designed.

Several systems have heretofore been developed for use in ophthalmic cataract removal, and phacoemulsification has become standard practice for removal of cataracts. In addition, "CUSA" (cavitation ultrasonic aspirator) systems have gained some currency among surgeons involved in neurological tissue resections. Ultrasonic equipment is also in current use for scaling (removal) of calcified plaque from teeth and for tissue emulsification and homogenization. All of the above-described devices are of limited applicability outside the particular context for which they were designed.

Ultrasonic devices have been employed for a variety of different applications outside the medical field as well. For example, ultrasonic apparatus has particular utility in the welding of plastics. Such equipment would also clearly be unsuitable for use in the context of surgery, where delicate living tissue must be carefully manipulated under sterile conditions.

U.S. Pat. No. 4,248,232 (Engelbrecht et al.) suggests the use of an osteotome for removal of osteal prostheses. This patent, however, is completely silent with respect to the type of osteotome which would be suitable for use in such a context. Moreover, the patent fails to indicate any parameters whatsoever for the use of an osteotome in orthopedic surgery. Therefore, it is not surprising that there has been no reported use of ultrasonic devices in the context of orthopedic surgery to date in the medical literature. In fact, since the issuance of U.S. Pat. No. 4,248,232 there has been a continued search for alternative techniques to solve the long-standing problems encountered in the removal of damaged prostheses, as well as in the implantation of new prosthetic devices. Accordingly, there remains a need for apparatus that would enable rapid and atraumatic removal of a prosthesis and/or the cement mantle surrounding same, as well as the safe and efficient implantation of prostheses.

SUMMARY OF THE INVENTION

There is disclosed in accordance with one aspect of the present invention, a method of removing an orthopedic prosthesis from a bone. Preferably, the prosthesis is a joint prosthesis of the type mounted in the medullary canal of the femur, and having a proximal body portion exposed outside of the bone, a distal stem portion extending within the bone, and a first axis extending from the proximal body portion to the distal stem portion.

In accordance with the method of the present invention, a source of ultrasonic energy is coupled to the proximal portion of the prosthesis. Ultrasonic energy is thereafter propagated from the source to the prosthesis, along a second axis, which extends within the range of no more than about 65° from a perpendicular to the first axis. Preferably, the second axis deviates from perpendicular to the first axis by no more than about 45°. More preferably, the second axis extends at approximately 45° from the normal to the first axis, or at approximately normal to the first axis.

In accordance with a further aspect of the present invention, there is provided a method of removing a joint prosthesis from a medullary canal. In accordance with the method, an ultrasonic transducer is coupled to the prosthesis and a sufficient ultrasonic signal is applied along a second axis of propagation to the prosthesis for vibrating the prosthesis and loosening it from the bone. The second axis of propagation extends within the range of from no more than about 65° away from a perpendicular to a first axis extending between the proximal and distal end of the prosthesis.

In one embodiment of the invention, the prosthesis comprises a porus surface secured with ingrown cancellous bone and the ultrasonic signal is sufficient for disrupting cancellous bone adjacent to the porus surface. In an embodiment where the prosthesis comprises a generally semispherical femoral head connected to the body of the prosthesis, the transducer is coupled to the femoral head. In an alternate embodiment wherein the prosthesis comprises a hole extending therethrough, the transducer is coupled to the prosthesis by way of the hole. Preferably, the ultrasonic signal has a frequency in the range of from about 20,000 to about 40,000 Hertz.

In accordance with a further aspect of the present invention, there is provided an adapter for connecting an ultrasonic energy source to a prosthesis, for receiving ultrasonic energy propagated along a first axis. The prosthesis has a second axis extending from a proximal end to a distal end thereof, and the adapter positions the first axis within the range from about no more than 65° away from a perpendicular to the second axis. Preferably, the adapter positions the first axis within the range of no more than about 45° away from the first axis.

These and further features and advantages of the present invention will become apparent from the Detailed Description of Preferred Embodiments which follows, when considered together with the attached drawings and claims.

BRIEF DESCRIPTION OF THE DRAWINGS

FIGS. 3A-3L illustrate novel adapters for use in extraction of hip femoral prostheses in accordance with the present invention.

FIG. 9 illustrates an alternative transverse mode adaptor for use with the prosthesis of FIG. 6.

FIG. 10 illustrates a further alternative transverse mode adaptor for use with the prosthesis of FIG. 6.

FIG. 11 illustrates a transverse mode variety of the adaptor illustrated in FIG. 3B.

DETAILED DESCRIPTION OF THE INVENTION

Figure 1:
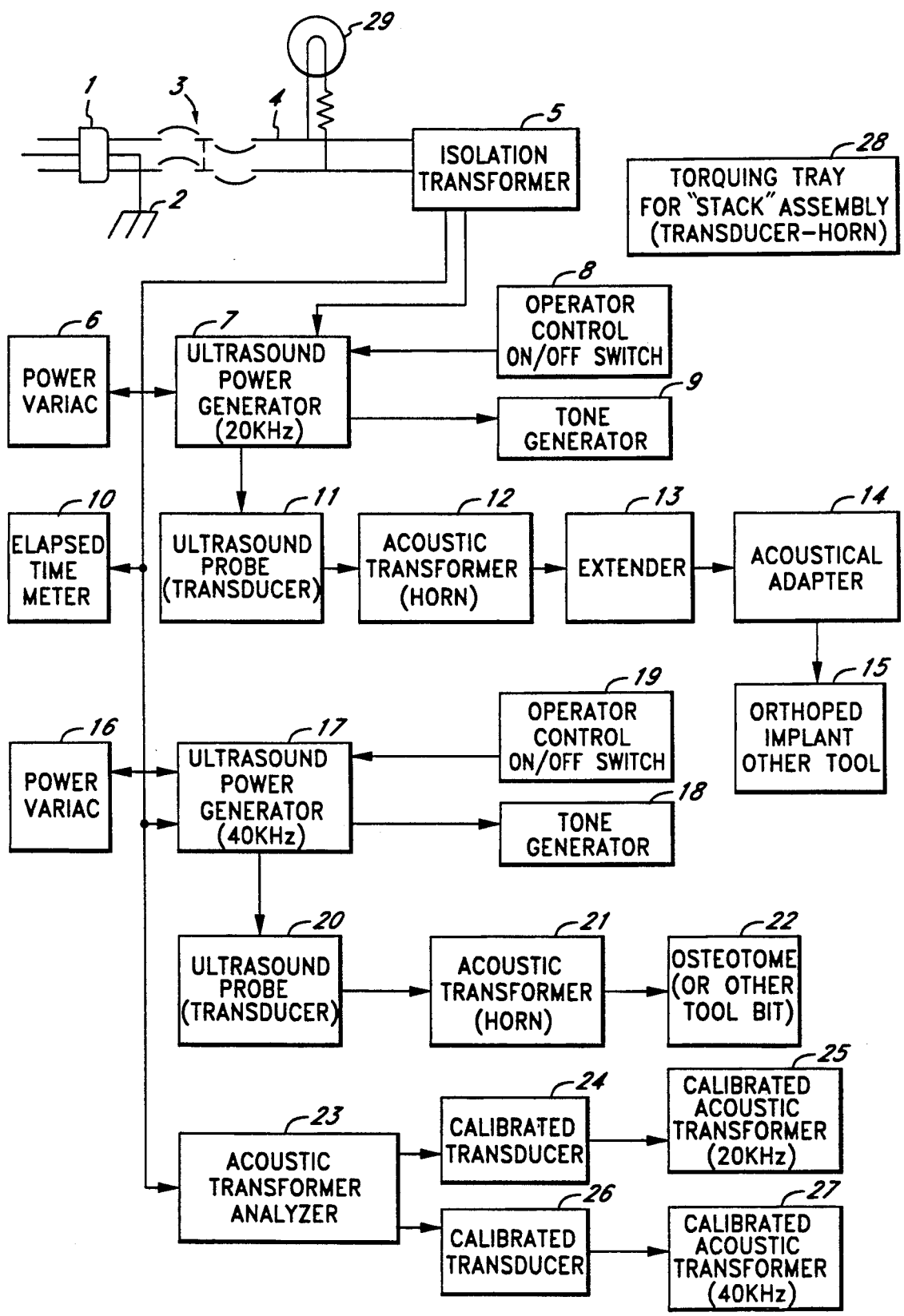
FIG. 1 illustrates in schematic form one embodiment of the inventive apparatus.

Referring to FIG. 1, there is provided in schematic form a description of one preferred embodiment of the apparatus in accordance with the present invention. A hospital grade AC electrical connector 1 (either 115 V or 220 V) is connected by means of low leakage AC power cable 2 to a dual circuit breaker 3 (preferably 15 A) of either the thermal or electromagnetic type. Cable 4 (generally a low-leakage AC power cable as customarily employed for internal wiring) connects circuit breaker 3 with an ultra isolation transformer 5 for leakage and AC line noise isolation. The transformer is suitably adapted for 110-230 V input (50-60 Hz). The transformer will ideally have a 1 kw rating, with less than 25.0 microamp leakage.

A regulator means 6 is provided, comprising in one embodiment a power variable auto-transformer (i.e., Variac) provided to adjust the power output limit. This device suitably has a nominal 10.0 A rating. In preferred embodiments, regulator means 6 comprises control means (for example, an appropriately programmed computer and associated hardware) for regulating the ultrasonic power generator in accordance with a predetermined algorithm. Regulator means 6 is connected to ultrasonic power generator 7, which preferably has a 20 KHz center frequency. While generators are available over the range of 500-2000 W, a 1 KW system is presently preferred. This is particularly the case because some well-embedded implants may require as much as 800 W for the first 1 to 5 seconds of removal. Higher power generators may be of advantage in some instances, because they provide a larger bandwidth of operation ($\pm 10\%$ of the center frequency) at reduced power output levels. This would permit less critical matching between the generator and other elements of the system, thereby making the system easier to use. A preferred ultrasonic power system is available from Dukane, St. Charles, Illinois under the designation ULTRA 1000 AUTOTRAC; equivalent systems may of course also be employed, suitably with 115 V input at about 13.0 ARMS maximum.

Control switch 8 is operative to turn on and off the high voltage generator output. A tone generator 9 is provided equipped with a commercially-available sound chip, amplifier and speaker. The tone generator 9 is operative to produce an indicator sound when the output from the ultrasonic generator 7 is on. A 60 Hz (or 50 Hz) AC elapsed time meter 10 is also provided for purposes of providing a maintenance history and for trouble shooting; a suitable time meter has an approximately 10,000 hour capacity and 0.1 hour indicator.

The high voltage generator output is connected to a transducer or ultrasound probe 11. The transducer 11 may be mounted in a handpiece (forming the transducer body) provided with a switch or operated by a medical grade footswitch. The transducer 11 may be sterilized using, e.g., ethylene trioxide; preferably, however, the transducer 11 is designed in a manner so as to be flash-steam autoclavable. Transducer 11 is designed to operate at 20 KHz (2 KW, ½ lambda). This transducer functions as a solid state linear motor. The transducer 11 converts electrical energy to a linear mechanical motion at 20 KHz frequency with an approximately 0.0008 inch peak-to-peak excursion. The mechanical output connection of transducer 11 is nominally a ½-20 set screw. At 20 KHz with this design and composition, ½ lambda is nominally 5.36 inches.

Acoustic transformer (sectional concentrator) or "horn" 12 increases or decreases the peak-to--peak motion (stroke/gain) of transducer 11. The acoustic transformer modifies not only the acoustic impedance, but also the quality factor Q. The quality factor defines a relationship between the damping factor and stroke versus the frequency shift. A high Q reflects high acoustical efficiency and minimal self-heating. Both the shape and the composition of the acoustic transformer affect Q; a straight conical acoustic transformer made of annealed 303 stainless steel, for example, would have a low Q, whereas a "stepped" horn of 7075-T6 aluminum would have a high Q. Generally, satisfactory horns are prepared from titanium or aluminum.

The length of the horn may vary greatly, depending on its design, composition and tuning frequency; typical lengths are on the order of 4.5 to 6.0 inches. For an exponential horn made from 7075-T6 aluminum, the nominal length would be 5.36 inches (½ lambda); the nominal wavelength (lambda) is the product of the density of the material and the speed of sound in the material.

Horn design is also determined by reference to the mode of operation. Thus, the shape of the horn will vary, depending on whether operations are carried out in exponential (low gain), catenoidal (medium gain) or stepped (high gain) mode. One particularly suitable acoustic transformer is a 6V-4AL titanium straight conical horn with a gain of approximately 3, for a 2.4 mil peak-to-peak stroke maximum.

The acoustic transformer 12 is mechanically-acoustically connected either directly or by means of an extender 13 to an adapter 14. Extender 13 serves the purpose of physically coupling adapter 14 to horn 12, as well as to assist in matching the frequency of the transducer 11 plus the horn 12 to the combination of the extender 13, adapter 14 and an associated tool or implant. In addition, extender 13 may offer temperature isolation between the adapter 14 and horn 12, particularly when extender 13 comprises titanium. One suitable composition is 6AL4V titanium. The extender 13 may be on the order of 1 to 6 inches in length.

Adapter 14 is used to connect the apparatus to an orthopedic implant (for implantation or extraction) or to individual tool bits for use in various surgical applications. The primary purpose of the adapter is to isolate the attached elements thermally while adjusting the nominal resonant frequency to 20 KHz±50 Hz.

As illustrated in FIG. 2, there are four basic types of hip femoral prosthesis in current use. Type 1 (FIG. 2A) comprises a stem 200 with a fixed ball arrangement 201; the ball generally has a diameter of 22, 26, 28 or 32 mm. A Type 2 prosthesis (FIG. 2B) has a so-called Morse taper stem 202; in addition, there is provided a horizontal extraction hole 203. The Type 3 prosthesis (FIG. 2C) comprises a Morse taper 204 and a vertical tapped hole 205. Finally, the Type 4 prosthesis (FIG. 2D) is provided simply with a Morse taper 206.

In accordance with one aspect of the present invention, novel adapters are provided which are expressly designed for use in conjunction with each of the four basic types of prosthesis depicted in FIGS. 2A-2D. The adapters are generally machined from stainless steel (e.g., 400 series), but may also be sintered, cast, etc. to the appropriate dimensions. Stainless steel is selected to lower the Q value at the implant interface while providing adequate strength to keep the adapter/implant interface from going into tension.

One suitable adapter for use in conjunction with a Type 1 prosthesis is illustrated in FIG. 3A. Adapter 300 comprises a base portion 301 provided with a recess 302, the diameter of which is matched closely to the diameter of the ball 201 of the corresponding Type 1 prosthesis. Suitably, the external circumference of base portion 301 is also provided with at least one recess 303 to provide clearance on the adapter 300 for a lower portion of the prosthesis 200. A plurality of cap screws 304 are provided in corresponding apertures 305 in the base portion 301. These cap screws 304 cause a high compression interference between the top of the ball 201 and the internal surface of adapter 300, as the faces of cap screws 304 contact the lower edge of ball 201 at some point below the midpoint of the diameter from the top of ball 201. In a typical arrangement, contact occurs at approximately ¾ of the diameter from the top of ball 201, whereby force is exerted at an approximately 45° vector. The cap screws 305 are generally not necessary when the adapter 300 is used for implanting. Connection means 306 is provided to permit facile assembly of adapter 300 with horn 12 and/or extender 13.

The adapter 310 illustrated in FIG. 3B is similarly designed for use in conjunction with a Type 2 implant. Base portion 311 is provided with a recess 312; portion 313 thereof is formed so as to provide a high compression fit between adapter 310 and the portion of the implant surrounding extraction hole 203. The upper portion 314 of recess 312 is designed to provide clearance for Morse taper 202. Cap screws 315 and corresponding apertures 316 in the base portion 311 are provided to engage extraction hole 203; generally, cap screws 315 are provided with tapered ends. Adapter 310 is similarly provided with attachment means 317.

FIG. 3C illustrates an adapter 320 of generally cylindrical shape for use with a Type 3 prosthesis. One end 321 is provided with an aperture 322 suitably machined to accommodate an end of a fastening means (such as a screw), the other end of which may be securely attached to the aperture 205 in the Type 3 prosthesis. End 321 is appropriately angled to provide clearance for the Morse taper 204 when adapter 320 is in place. An opposite end 323 is provided with an aperture 324, also suitably machined to permit coupling with the horn 12 and/or extender 13. To facilitate attachment and removal of adapter 320, a pair of indentations 325 (one of which is illustrated) are provided on the surface of the generally cylindrical body; indentations 325 suitably present a flat surface for secure engagement of adapter 320 by a wrench or other appropriate tool.

For use with a Type 4 prosthesis, adapter 330 (FIG. 3D) comprises a base portion 331 provided with an offset through hole 332 at an angle to match that of the Morse taper 206. Generally, the angle of the Morse taper is on the order of 135°; through hole 332 is matched to this angle, and offset sufficiently to match the taper in a line-line fit. A plurality of apertures 333 are provided on the circumference of base section 331 surrounding through hole 332 for insertion of some type of fastening means (e.g., set screws) to secure Morse taper 206 in place in through hole 332. In addition, the use of a suitable adhesive to fix Morse taper 206 in place may be advantageous. In a typical extraction procedure, adapter 330 is brought into engagement with Morse taper 206 and seated firmly, for example by tapping on surface e of adapter 330. After the setting of adhesive or other fixing agent, if any, employed to secure engagement of Morse taper 206, fastening means introduced through apertures 333 are brought into contact with morse taper 206 so as to further strengthen the attachment of adapter 330 during the extraction procedure. Once again, neither a fixing agent nor fastening means would be necessary when the adapter is used for implantation of a prosthesis.

FIG. 3E illustrates a modified adapter 340 designed for use with a Type 1 prosthesis, and particularly suitable for implantation. While lower portion 341 is again provided with an aperture 342 designed to accommodate the ball portion 201 of the Type 1 prosthesis, the adapter 340 is further secured by means of a split nut 343, which obviates damage to the ball portion 201 of the prosthesis as might result from the use of a screw-type attachment. A bottom portion of split nut 343 with a half cup matching the diameter of ball portion 201 is first snapped into place on the prosthesis; adapter 340, including a top portion that mirrors the split nut 343, is then applied over the prosthesis and the halves of split nut 343 brought into engagement. To ensure a good alignment of the halves of split nut 343, one or more pins which are inserted into match-drilled holes may be used. Once again, connector means 344 is provided for secure engagement with horn 12 and/or extender 13.

Acoustic transformer 12, extender 13 and adapter 14 may suitably be coated with anodized (tiodized) processing, or using titanium nitride or boron nitride. Through the use of specific color coatings and/or identification codes, as well as standardized fittings for all components, the interchange of adapters and extenders for use with a variety of orthopedic implants and tool bits is rendered simple and essentially error-proof.

For implantation or removal of orthopedic prosthesis, a direct mechanical/acoustical connection is made via the appropriate adapter. While the adapters are of four basic types, variations are provided to accommodate the differences encountered among the commercially available prostheses with respect to implant angle, dimensions, ball size, hole size and composition. To facilitate use by the surgeon, the system is designed so that it is necessary merely to identify the particular type of prosthesis involved, whereupon the appropriate adapter (and, if needed, extender) may be selected from among those provided with the apparatus.

Figure 5:
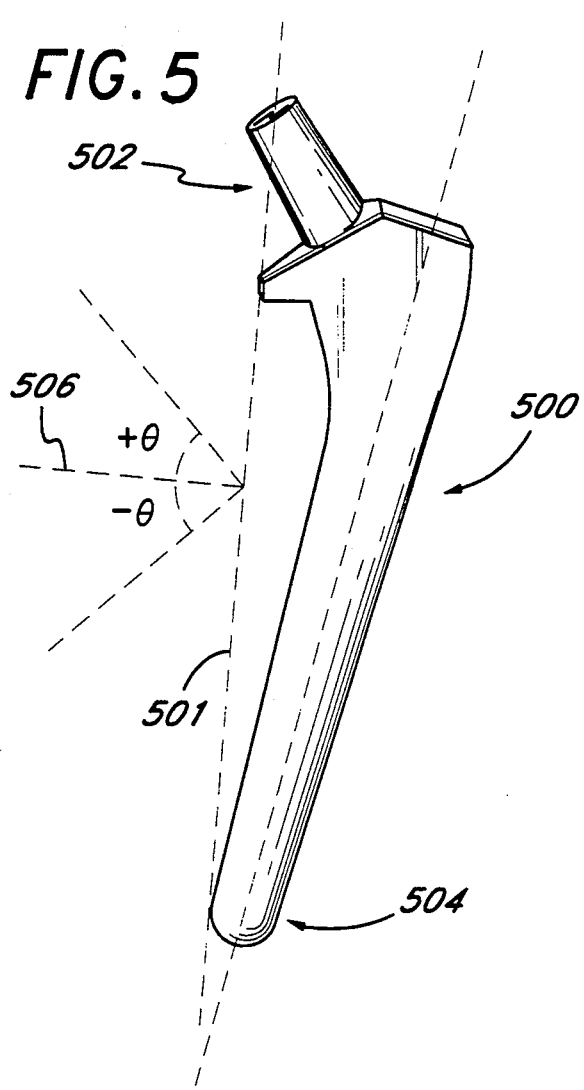
FIG. 5 illustrates the incidence angle of ultrasonic energy with respect to a prosthesis in accordance with a transverse mode of the present invention.

The foregoing adapters are generally designed to co-propagate ultrasonic energy along an axis which is co-extensive, parallel or nearly parallel to the chord 501 extending between the proximal end 502 and distal end 504 of the prosthesis 500, as shown in FIG. 5. When the prostheses are driven parallel to the cord, the length, material, shape, modulus of elasticity and speed of sound in the material, all have to be accommodated when driven ultrasonically. In accordance with a further aspect of the present invention, adapters are provided for propagating ultrasonic energy along an axis which is generally transverse to the chord 501 on prosthesis 500. In many applications, it may be preferable to introduce the waves along an axis 506 perpendicular to the chord 501, or along an axis which deviates from the normal axis 506 by an angle $\theta$ which is no more than about 65° and preferably no more than about 45°. As used herein, "normal" or "perpendicular" shall refer to an axis 506 extending at a 90° angle with respect to chord 501, and "transverse" shall refer to an axis within the range of from about −45° to about +45° with respect to normal axis 506. It should be understood that the normal axis 506 may lie anywhere in the plane perpendicular to the chord 501.

Introducing the waves along the normal axis 506 causes the prosthesis 500 to act primarily as a load. In some applications this may assist the surgeon by making set-up and use easier.

Introducing the waves along an axis which deviates from the normal axis 506 by an angle 8 tends to cause the prosthesis to move in an elliptical pattern. In some applications, this may assist the surgeon in breaking bonds formed between the prosthesis and the natural bone. In addition, deviation from the normal axis 506 imparts a vector component of force in either a proximal or distal direction, which can assist in implantation or withdrawal of a prosthesis.

Figure 6:
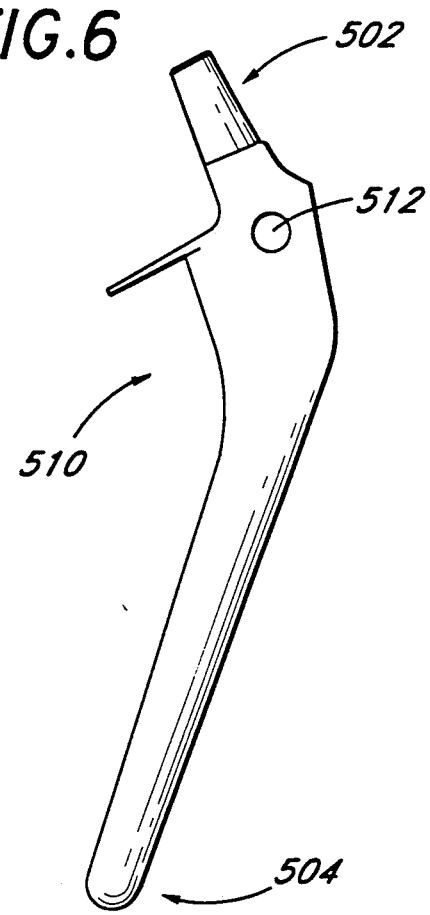
FIG. 6 illustrates a hip prosthesis.
Figure 8:
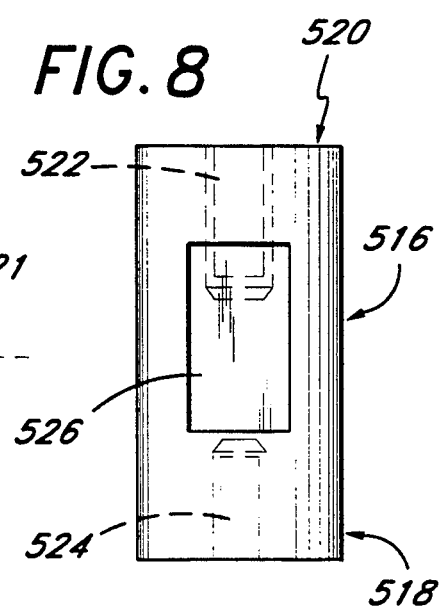
FIG. 8 illustrates a transverse mode adaptor for use with the prosthesis illustrated in FIG. 6.

FIG. 6 illustrates one embodiment of a prosthesis for use with the present invention in which, in combination with the adapter of FIG. 8, the ultrasonic waves are introduced along an axis perpendicular to the chord connecting the proximal end 502 and distal end 504 of the prosthesis 510. In this embodiment, the prosthesis 510 has a hole 512, the longitudinal axis of which is perpendicular to the prosthesis chord 501.

A source of ultrasonic energy is coupled to the prosthesis 510 by way of hole 512 in any of a variety of ways. For example, hole 512 can be provided with a tap for receiving a threaded male component coupled to an ultrasonic transducer. Removal of the prosthesis from the femur is in this embodiment accomplished by surgically exposing at least one side of the prosthesis 510, and connecting the transducer by threading the male component within the hole 512.

The adapter 516 can be provided with a variety of additional connection means for connecting to either the ultrasound source or the prosthesis. One such connection means is the spline key way structures disclosed in U.S. patent application Ser. No. 665,418, filed Mar. 5, 1991, the disclosure of which is incorporated herein by this reference.

Alternatively, the prosthesis 510 is coupled to a source of ultrasonic energy by way of an adaptor such as illustrated in FIGS. 8-11. Referring to FIG. 8, there is disclosed an adapter 516, which comprises a material suitable for ultrasonic energy propagation. Adapter 516 is provided with a prosthesis coupling end 518 and a transducer coupling end 520. Prosthesis coupling end 518 further is provided with a tapped bore 524 for receiving a threaded rod (not illustrated). The threaded rod is inserted in the bore 524 in such a manner that it extends out of the adapter 516 a sufficient distance to extend all the way (if bore 512 is not threaded) or at least part way (if bore 512 is threaded) through the length of the bore 512 in prosthesis 510. Alternatively, the threaded rod is rigidly affixed to or integrally formed with the adapter 516. Adapter 516 is mounted on the prosthesis 510 by extending the threaded rod through the hole 512 and securing a bolt on the distal end of the threaded rod.

The ultrasonic transducer coupling end 520 of adapter 516 is provided with a structure for coupling the adapter 516 to a source of ultrasonic energy. In one embodiment, a bore 522 is provided with a female thread, for engaging a male thread which is coupled to the ultrasonic transducer. A pair of opposing flats 526 is provided on the adapter 516 for receiving a wrench, to assist in tightening the connections between the adapter 516, the prosthesis 510, and the ultrasound source.

As a further alternative, the adapter 516 can be modified in any of a variety of ways to introduce ultrasonic energy along an axis which deviates by an angle $\theta$ from the normal axis 506 to the chord 501. For example, referring to FIG. 9, there is disclosed an adapter 540, having a prosthesis contacting surface 541 extending in a plane inclined at an angle $\theta$ from a perpendicular to the longitudinal axis of the adapter. The adapter 540 further is provided with a tapped bore 545, having an axis 550 perpendicular to the prosthesis contacting surface 541. Referring also to FIG. 6, the adapter 540 is then attached to the bore 512 in the prosthesis 510 in any suitable manner as described in connection with the adapter 516 of FIG. 8. Ultrasonic waves are then introduced via face 552 at an angle $\theta$ relative to the normal 506 of axis 501.

As will be apparent to those skilled in the art, the angle $\theta$ at which the ultrasonic energy is introduced may also be modified by including an elbow bend in any of the adapters heretofore discussed.

Thus, for example, referring to FIG. 10, there is disclosed an adapter 555 having a predetermined angle $\theta$ for introducing ultrasonic energy along an axis which is generally transverse to the chord 501 in the context of FIG. 5. Adapter 555 is provided with a prosthesis contacting surface 556, and an ultrasonic energy coupling surface 558 as have been previously described. In addition, adapter 555 is provided with a predetermined angular bend 560, to offset the plane of the prosthesis contacting surface 556 from parallel with the plane of the ultrasonic energy source coupling surface 558.

Coupling of the adapters 540 and 555 to a prosthesis such as 510 illustrated in FIG. 6 can be accomplished such that the ultrasonic energy is propagated along an angle which is either $+\theta$ or $-\theta$ in the context of FIG. 5, by rotating the adapter through an angle of 180° about the axis of bore 512 as will be readily apparent to one of skill in the art.

In still another embodiment of the present invention (not illustrated), the prosthesis is prepared with a hole, the longitudinal axis of which deviates from the normal of the prosthesis chord. Any of the above-described apparatuses and methods may then be used to introduce the ultrasonic energy along an axis perpendicular to the prosthesis chord, or along an axis which deviates from the normal by a specified angle.

In many applications, the prosthesis will not contain a hole to which an ultrasonic tool may be coupled. Nevertheless, it remains possible to introduce the ultrasonic energy at the desired angle through the use of specially modified adapters.

Figure 2A:
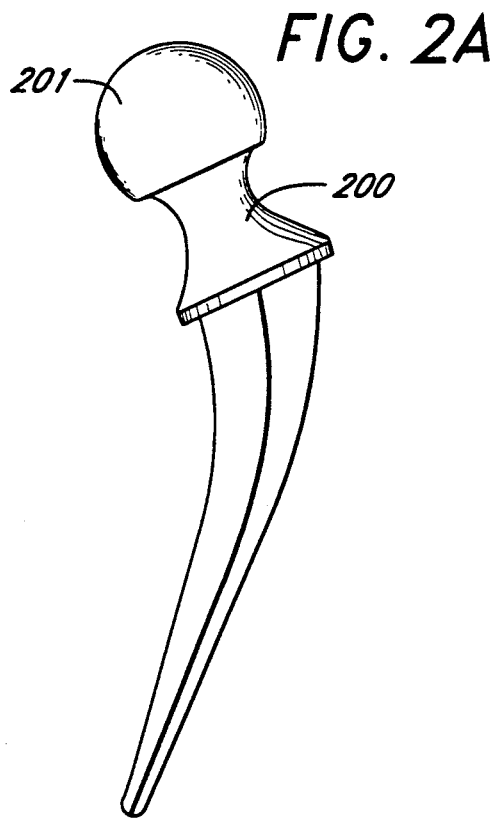
FIGS. 2A-2D illustrate four basic types of prior art hip femoral prostheses.
Figure 2B:
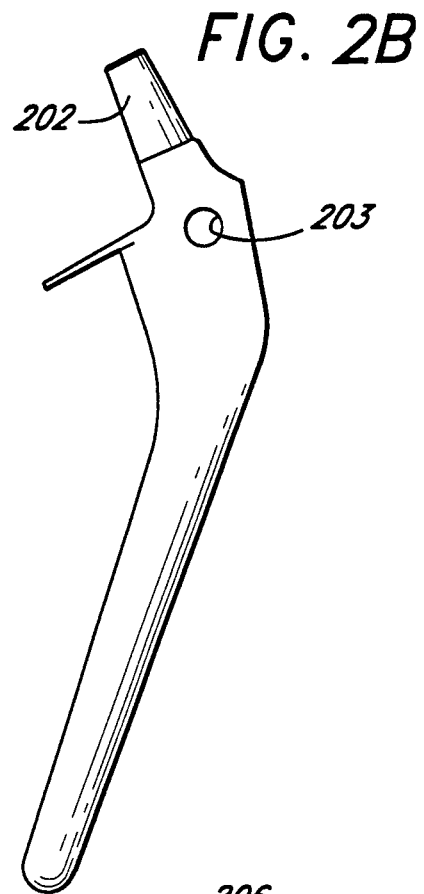
Figure 2C:
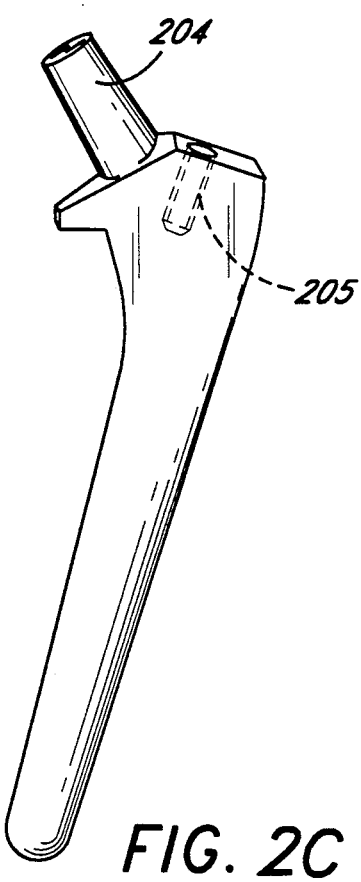
Figure 2D:
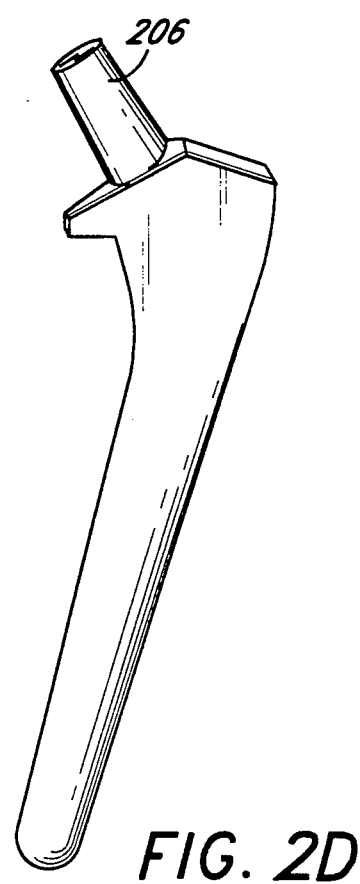
Figure 7:
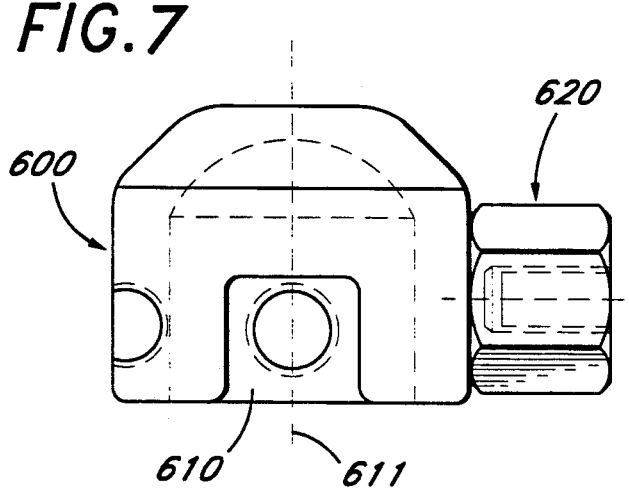
FIG. 7 illustrates a transverse application adaptor for use with a prosthesis of the type illustrated in FIG. 2A.

Referring to FIGS. 2A and 7, a prosthesis of Type 1 and an adapter 600 are illustrated. The adapter 600 is a modified version of the Type 1 adapter shown in FIG. 3A. The adapter 600 contains a ball recess 610 designed to receive the ball 201 of the Type 1 prosthesis. The adapter 600 further comprises a transducer coupler 620. In this embodiment, the axis 621 of the transducer coupler 620 is perpendicular to the axis 611 of the recess 610. The adapter 600 is inserted over the prosthesis ball and rotated until the axis 621 of the transducer coupling end 620 forms the desired angle with the chord connecting the near and distal ends of the prosthesis. The adapter 600 is then fastened in the manner described in connection with the adapter shown in FIG. 3A.

As will be apparent to those skilled in the art, this embodiment may be modified by positioning the axis 621 of the transducer coupler 620 at any alternative angle relative to the axis 611 of the ball recess 610. As will also be apparent to those skilled in the art, an elbow bend can be incorporated into the joint between the main body of adapter 600 and the transducer coupler 620, further modifying the ultimate angle at which the ultrasonic energy is introduced relative to the prosthesis chord.

In another embodiment, a modified adapter of Type 2 is used. Referring to FIG. 11, the adapter 680 has a prosthesis contacting surface 681 extending in a plane at an angle deviating from the perpendicular to the incidence propagation axis of the adapter. The adapter 680 is further provided with a bore 682 having an axis 683 perpendicular to the contacting surface 681. In all other respects, the bore of this embodiment is identical to that described in connection with FIG. 3B. The Morse taper of a Type 2 prosthesis is then inserted into the adapter 680, and the adapter is rotated until the desired angle is achieved. In addition, or in the alternative, an elbow bend can be included in the adapter 680 to modify the angle at which ultrasonic energy will be introduced.

Though only inclined adapters for certain prostheses have been discussed, it will be apparent to those skilled in the art in view of the disclosure herein that similar adjustments can be made in other adapters to allow for the introduction of ultrasonic energy along an axis perpendicular to the prosthesis chord, or along an axis deviating by an angle of $\theta$ from the perpendicular to the prosthesis chord.

Finally, it should be understood that in some applications it may be desirable to use two or more adapters during the same surgical procedure. Alternatively, it may be desirable to shift a single adapter, for example, from a $-\theta$ orientation to a $+\theta$ orientation during a procedure. As just one example, it may be desirable to begin a prosthesis extraction by using an adapter which introduces the ultrasonic waves normal to the chord 501, and then using an adapter which introduces the ultrasonic waves along an axis which deviates from the normal, imparting a vector component in the proximal or distal direction.

Thus, there is provided in accordance with one aspect of the present invention a method for removing a prosthesis from a bone. Typically, the prosthesis will be a prosthetic hip joint having a stem for extending within the femur. In this application, the prosthetic hip joint will typically be cemented to the bone, utilizing a cement such as PMMA. Alternatively, however, the method of the present invention may be utilized to disrupt any of a wide variety of prosthesis-to-bone bonds.

In accordance with the present invention, a source of ultrasonic energy is coupled to the proximal portion of a prosthesis. The prosthesis is of the type having a proximal body portion exposed outside of the bone, a distal stem portion extending within the bone, and a first axis extending from the proximal body portion to the distal stem portion.

Ultrasonic energy is propagated from the source to the prosthesis, along an axis of propagation which extends generally transverse to the first axis. Thus, the axis of propagation may be either precisely perpendicular to the first axis, or the axis of propagation deviates within the range of from about 45° or less from the perpendicular to the first axis.

Following or during propagation of ultrasonic energy from the source to the prosthesis, the prosthesis is removed from the bone.

In accordance with another aspect of the present invention, ultrasonic energy is first propagated along a second axis which is perpendicular to the first axis of the prosthesis, to disrupt the prosthesis from the surrounding PMMA or bone. Thereafter, the ultrasonic energy is propagated along a third axis which deviates from the second axis, during the removal of the prosthesis from the bone or both can be driven at the same time, with a highly amplified effect. A 10-1000 Hz difference in frequencies would be very effective, with 100 Hz preferred. This aspect of the present invention can be accomplished by propagating energy in the first step by way of a first adapter into the prosthesis, and thereafter withdrawing the first adapter and mounting a second adapter for propagating ultrasonic energy along the third axis. Alternatively, the propagation of ultrasonic energy can be switched from a first incidence angle to a second incidence angle by rotating the adapter about an axis which extends through the prosthesis.

Referring now to FIG. 1, a separate circuit comprising power auto-transformer 16, ultrasonic generator 17, tone generator 18, on/off switch 19, transducer 20 and acoustic transducer 21 is provided for purposes of operating an osteotome 22 or other tool bit. The elements 16-21 are of comparable design and construction as those of the first circuit described above, except that power auto-transformer 16 is designed to have a 6 A maximum rating, and transducer 20 operates at 40 KHz (700 W; ½ lambda=2.68 inches). Osteotome 22 is generally of stainless steel or titanium, and is used for modifying tissue or plastic; various shapes and sizes are provided for use as gouges, curettes, drills, etc.

A calibration circuit is provided, comprising an acoustic transformer analyzer 23, a calibrated transducer 24, a calibrated acoustic transformer 25 (aluminum, precision calibrated to 20 KHz±20 Hz), a second calibrated transducer 26 and a second calibrated acoustic transformer 27 (precision calibrated at 40 KHz±40 Hz). A preferred acoustic transformer analyzer is the Dukane Model 40A350 analyzer. The calibration circuit allows for testing and calibration of elements 11-15 and/or 20-22 in whole or in part.

A torquing tray 28, generally in the form of a stainless steel tray and hold down clamps, is provided to hold the transducer firmly while assembling the various components attached thereto (i.e., the acoustic transformer, adapter/extender and the tool element). An indicator lamp 29, preferably with a voltage/current limiting resistor, advises the operator when the apparatus is on.

Operation of the system is effected as follows. For an identified prosthesis, the appropriate combination of horn, extender (if necessary) and adapter is selected. Using torquing tray 28 and suitable wrenches, the combination of horn/extender/adapter is assembled and connected with the transducer. The assembly is then connected to the prosthesis. A low power output (corresponding to a reduced stroke of, e.g., 20%) is selected for operation in a test mode and the range control is adjusted for a minimum power reading on the power meter. If the reading is greater than, e.g., 100 W, adjustment is necessary before proceeding; in general, adjustment of the frequency to 20025±50 Hz (for example, by change of extender) is sufficient to provide an acceptable power reading at low stroke.

Explanation may be effected by application of a satiable traction force (e.g., 10 pounds) on the transducer body housing and activation until the prosthesis has been removed (30 seconds maximum). Implantation into a femur bed already prepared for an interference fit similarly calls for application of compression force, with activation until the prosthesis is fully seated. Automatic adjustment of operating parameters is effected in a manner known per se by suitable circuitry provided within the ultrasonic generator equipment. The ultrasonic generator is designed to maintain a constant stroke. If the transducer encounters substantial clamping or holding forces, the ultrasonic generator provides additional power (up to its output limit) to keep the stroke constant. Similarly, an internal frequency control maintains a fixed phase relationship between the driving voltage and the current, to adjust for shifts in frequency due to loading. Preferably, the ultrasonic generator is designed to provide a "soft-start" feature, whereby initial stress on the transducer and drive elements is reduced.

Well over 100 different types of orthopedic implants are currently available for use in reconstruction of the hip, knee, elbow, shoulder, wrist, finger, toe, ankle, neck, etc. The inventive apparatus is designed to accommodate all of these various types of implants, simply by interchanging the adapters (and, where necessary, by using in addition the appropriate extender). Further, the apparatus may be used in conjunction with various types of T-bars (for use in removal of bone marrow), broaches, files, gouges and curettes. In fact, virtually any type of surgical tool (including those driven by hand, mallet, pneumatically, electrically or hydraulically) can be adapted for use with the present invention. Most metallic, ceramic and plastic orthopedic implants (including those fixed with bone cement and porous types with substantial bone ingrowth) may be extracted or inserted into bone. Pins and rods used for bone fixation may be driven with the inventive apparatus, as may cutting or coreing cannulae and curettes for bone, tissue or plastic modification. The inventive apparatus may further be used for purposes of ultrasonic debriding. In addition, the apparatus may be used (with modified and new adapters) for dental implants, cosmetic surgery, Ob-Gyn and neurosurgical applications, etc.

In preferred embodiments, the workpiece may further comprise an irrigation/aspiration system with switch-over valves to an available hospital air vacuum line and/or a biopsy trap. For purposes of fine bone and/or tissue resection, a smaller handpiece is provided. Pneumatic-guillotine cutters (e.g., occutomes, nucleotomes, biotomes, etc.), endoprobe accessories with camera capabilities and illuminators (ideally with disposable optical fiber cables) are additional elements of the system available for particular uses. In addition to ultrasonic knives (with adjustable sharpness and drag), "hot knives" and/or uni- or bi-polar cautery electrosurgical knives may be provided.

A significant feature of a preferred embodiment of the present invention is the use of either a touch screen CRT or flat panel display to input control and data functions. In addition, the display/control system displays all systems parameters and performs the selection of appropriate adapters and/or extenders for a particular use. The system is ideally designed for infrared remote control from a sterile field and/or voice control of all system functions. In a further preferred embodiment, patient data and procedure parameter storage may be accomplished using diskettes (e.g., "floppy" disks) compatible with office or hospital computer systems. A bar code reader system may be employed. Magnetic or optical cards or disks may alternatively be used for input and/or storage of information. Repair or systems verification tests may ideally be carried out by means of modem capability of the control system.

In general, the algorithm for implantation or explanation of a particular prosthesis is initially determined empirically, in view of the complex shape of each adapter/prosthesis combination and the widely varying acoustical performance of each of the range of prostheses currently available. Once the appropriate operating parameters have been determined, this information is incorporated into the system memory so as to permit ready access by the operator/surgeon. Thus, for example, in one type of embodiment of the inventive apparatus, the operator would select the manufacturer and part number corresponding to the prosthesis in question. A display associated with the apparatus could provide an illustration of an actual-size implant for comparison purposes (e.g., with a patient X-ray) and/or identify the appropriate horn, extender and adapter for use in conjunction with the given prosthesis. Alternatively, the necessary information concerning the appropriate combination of elements for a given prosthesis could be recovered manually (e.g., using charts or tables).

To determine the appropriate configuration for any given prosthesis empirically, a first test adapter is machined to match a given implant. One of a series of standard calibrated extenders (for example, varying in length over a range of 1 to 5 inches in 0.125" increments) is attached to the adapter and to a low gain (exponential) test horn. This assembly is then attached to analyzer means and the frequency noted. In the event of a discrepancy between the measured frequency for the assembly and the target frequency at 20025 ±25 Hz, the extender is changed and/or a new adapter is machined to an appropriate length; in practice, a difference in length of 0.001" corresponds to about 1.866 Hz. This process is repeated until frequency parameters are met.

The assembly is then attached to a calibrated power generator and transducer. At 100% stroke, the power should be less than 50 watts in free air and the stroke 1.5–4.5 mils (0.0015") peak-to-peak nominal. If the stroke is not greater than 1.0 mils peak-to-peak at all points along the stem of the implant, the horn design is modified to increase the gain.

Following the above-described procedure, it is possible to determine the ideal operating parameters for insertion or removal of any prosthesis, as well as for surgical operations using any type of tool attachment. As an example, it has been determined that explanation of a Charnley-Mueller 32 mm fixed ball total hip prosthesis required 150 watt output at an approximately 2.0 mil peak-to-peak stroke for 7 seconds; this procedure resulted in a temperature increase in the adjacent bone of less than 3° C. Implantation of the same prosthesis requires about 175 watts at the same stroke for about 3 seconds, and results in a temperature increase of about 5° C. or less. Removal of PMMA bone cement using a curette (for example, a modified Zimmer 3670 curette) requires a maximum of 125 watts at an approximately 1.5 mil peak-to-peak stroke; approximately 2 mm of material is removed per second with a temperature rise of about 7° C. or less.

In the development of the present invention, alternative technologies for explanation were also considered. One alternative was the use of an electric current source with carbon-graphite electrodes attached across an exposed metal prosthesis, whereby the heat of the current flow across the resistive metal prosthesis would eventually heat the entire prosthesis until the PMMA cement would soften and release the prosthesis. Another alternative was the use of focused ultrasound (5–100 KHz) on the centerline of the prosthesis. The energy directed from a trough-shaped or phased array of piezoceramic elements would be transmitted into the tissue through a water bag technique as presently in use for lithotripsy. A large angle, short focal length transducer slope would minimize localized tissue heating. Yet another alternative contemplated was a modified water-cooled RF welder (3 KW, 450 KHz); a special ("welding/brazing") coil shaped to selectively heat the stem portion of a prosthesis until the PMMA interface softened.

The invention will be better understood by reference to the following examples which are intended for purposes of illustration and are not to be construed as in any way limiting the scope of the present invention, which is defined in the claims appended hereto.

EXAMPLE 1

Prosthesis Insertion and Removal

This experiment was designed to determine the effects of ultrasonic tools and energy on endosteal bone during prosthesis and cement removal. Thermal necrosis is a common problem with various orthopaedic procedures. Temperatures above 47° C. have been shown to create irreversible bone injury in vital microscopic studies, and alkaline phosphatase denatures at 56° C. Unfortunately, temperatures as high as 100° C. have been recorded during in vitro drilling of cortical bone. To demonstrate that the apparatus of the present invention permits a safe and rapid execution of the desired surgical procedures without substantial risk of tissue necrosis, heat generation was thoroughly investigated according to the following procedure.

Figure 4:
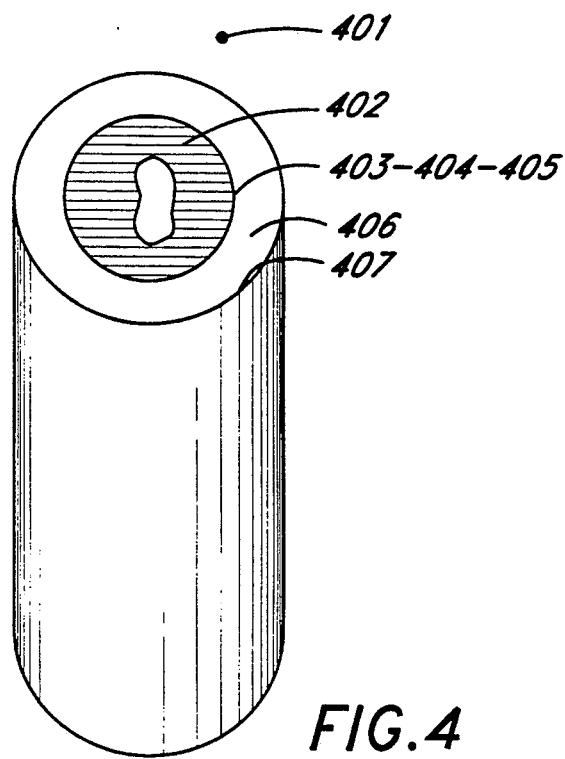
FIG. 4 illustrates the location of thermocouple sites on a cadaveric femur as employed in determinations of temperature during application of ultrasonic energy.

Ten cadaveric femurs, fresh frozen at −10° C. for 2–5 weeks, were thawed to 37° C. Thermocouple wires Type J (20 gauge) were inserted using a 2.0 mm AO drill provided with a cortical depth caliper, and silicone sealant applied to isolate the brazed tips from the water bath. Seven thermocouple sites 401–407 were employed, as illustrated in FIG. 4. Temperature and time were recorded on a 12 channel Graphtec Strip Chart Recorder (Model No. WRB 101/120), Tokyo, Japan. All channels were normalized to 37° C.; calibrations were effected at room temperature, 37° C., 46° C., and 55° C. using suitable standard laboratory thermometers before all trials, after the third trial, and at the end of all trials.

During the prosthesis insertion and removal procedures, a 40 liter galvanized tank provided with a double screw holding clamp and filled with 0.9% (normal) saline was used as a water bath. The bath was heated and maintained at 37° C. using a heat flow pump (Model No. 73T available from Polyscience Corp., Niles, Illinois. Poly(methyl methacrylate) cement (Howmedica, Rutherford, New Jersey) was prepared according to the manufacturer's instructions. A 32 mm fixed head Charnley prosthesis with a double-tapered stem was inserted into each femur; a 2-4 mm cement mantle was retained.

Temperature measurement began with prosthesis insertion. After curing of the bone cement and adjustment of the cement core temperature to 37° C., each prosthesis was removed using the apparatus of the present invention, operating at 200 Watt maximum power output and 100% stroke. The forces required for removal of the prosthesis were measured using a standard 100 pound spring-type hand-held tension gauge.

In all trials except a final one, the ultrasonic coupler/prosthesis interface was tightly secured, in order to ensure efficient energy transfer and minimize the total energy requirements during removal. In the final trial, interface failure was created in an attempt to evaluate a hypothetical situation resulting in prolonged heating and ultrasonic energy transmission. After prosthesis removal, a 2.5×2.5 cm area of cement mantle surrounding the proximal thermocouple was removed using ultrasonic curettes and gouge, until all of the underlying bone was exposed. Temperatures were recorded throughout the removal process. Three control femurs were prepared in a similar fashion; the prostheses were inserted over a thin plastic sleeve and the prosthesis manually removed after cement curing.

Temperature measurements at the thermocouple sites during cement curing and prosthesis removal are reported in Table 1. The mean $T_{max}$ (° C.) recorded at all bone cement interface leads was 39.0 during ultrasonic removal of the prosthesis, as compared to 39.9 during cement curing. The cement core mean $T_{max}$ (° C.) was 40.8 during prosthesis removal, as compared to 47.9 during cement during. The highest recorded cement core temperature during ultrasonic removal of a prosthesis was 43.1° C., as compared to a high of 66.3 recorded during cement curing. Temperature elevations at am id-cortial and periosteal leads were considered negligible (<2° C.) throughout.

The mean pull-out force required for ultrasonic removal of a prosthesis was 10 pounds; the range of forces was about 8-12 pounds. The mean time required for prosthesis removal was 9.7 seconds; the range of times was about 4.2-21.0 seconds.

During the trial in which ultrasonic coupler/prosthesis failure was deliberately induced, the mean bone cement/interface $T_{max}$ was 46.5° C. Even under these unfavorable conditions, the mean pull-out force was only 22 pounds, and the time required for prosthesis removal 39.7 seconds.

The 10 human cadaveric femurs were preserved in 10% buffered formalin for 10 days prior to routine decalcification, preparation with hematolyxin and eosin, and sectioning for pathologic analysis by an experienced bone pathologist. Attention was directed to the degree of induced osteonecrosis and thermal injury which occurred during prosthesis removal (7 femurs), compared to the three controls.

Gross inspection of all specimens revealed no evidence of thermally induced eburnation of cortical bone. Curetted sites also revealed no evidence of cortical scarring.

Each specimen was analyzed by light microscopy for evidence of cellular destruction in cortical lacunae and/or altered staining patterns indicative of thermally induced matrix damage. The depth of cortical bone damage was calibrated microscopically at all interface thermocouple levels.

The mean depth of cortical damage at the cement cortical interface was determined to be 6.1 micrometers (0.0-12.0 micrometers). The mean depth of cortical damage at the curette sites was 7.0 micrometers (4.0-9.0 micrometers). The mean depth of cortical damage at the curette sites was 7.0 micrometers (4.0-9.0 micrometers). Even in the trial where direct coupling to the prosthesis was deliberately suboptimal, the mean depth of cortical damage was only 14.2 micrometers (7-17 micrometers). The controls had a mean depth of cortical damage of 2.0 micrometers (0.0-3.0 micrometers).

The results confirm that direct coupling to a well-fixed, cemented prosthesis with an ultrasonic tool allows for rapid and atraumatic extraction of the prosthesis and rapid removal of the retained cement mantle without significant cortical damage. Maximum temperatures generated were far below those which generate thermal necrosis. No evidence was found of microfracture from ultrasonic energy transmission, and minimal cell injury was observed on a microscopic level. The efficiency of this technique of prosthesis removal is demonstrated by the short pull-out times and low pull-out forces required.

EXAMPLE 2

Ultrasonic Removal of Bone Cement

Eight freshly harvested canine long bone specimens (four humeri, four femoral) were prepared by exposing the intramedullary canals at the epiphysealmetaphyseal junction. The canals were broached in a standard fashion. Polymethyl methacrylate cement was prepared and digitally packed into the intramedullary canals. After curing of the cement, the specimens were allowed to harden at 10° C. for 72 hours. Ultrasonic tools were then used to remove the cement completely from an interior portion of the cement-filled area.

The bone specimens were sectioned using a diamond tip microtome into 1 mm thick disks at points near both ends of the portion from which the bone cement had been removed, as well as from a control point remote from the cement-filled area. The disks were then prepared for microradiographs and electron micrographs (20 KV, 10x). The microradiographs and electron micrographs of all disks demonstrated the preservation of normal bony architecture.

From the foregoing description, one skilled in the art can readily ascertain the essential characteristics of the invention and, without departing from the spirit and scope thereof, can adapt the invention to various usages and conditions. For example, novel problems have arisen with porous ingrowth prostheses, and removal thereof can be a highly morbid procedure involving a proximal femoral osteotomy. Early clinical applications of the present invention have provided promising results with respect to the role of ultrasonic tools in porous growth revision arthroplasty. Changes in form and substitution of equivalents are contemplated as circumstances may suggest or render expedient, and although specific terms have been employed herein, they are intended in a descriptive sense and not for purposes of limitation.

TABLE I

| Mean Temperature at Thermocouple Sites for Human Femoral Trials | | | |
|---|---|---|---|
| Thermocouple Site | Cement Curing | Ultrasonic Pull-Out | Ultrasonic Curetting |
| Proximal | 40.3 | 38.9 | 38.7 |

TABLE I-continued

| Thermocouple Site | Mean Temperature at Thermocouple Sites for Human Femoral Trials | | |
|---|---|---|---|
| | Cement Curing | Ultrasonic Pull-Out | Ultrasonic Curetting |
| Interface Mid-Prosthesis | 39.5 | 39.4 | — |
| Interface Distal | 39.9 | 38.8 | — |
| INTERFACE AVERAGE | 39.9 | 39.0 | — |
| Mid-Cortex | 38.1 | 37.4 | — |
| Periosteal Surface | 37.4 | 37.6 | — |
| Cement Core | 47.9 | 40.0 | — |

Although this invention has been described in terms of certain preferred embodiments, other embodiments that are apparent to those of skill in the art in view of the foregoing disclosure are also within the scope of the invention. Accordingly, the scope of the invention is intended to be defined only by reference to the appended claims.

What is claimed is:

1. An adaptor for connecting an ultrasonic device to a prosthesis including a ball having a given diameter at an exposed end thereof and a lower portion of the prosthesis, said adaptor comprising:

a base portion having an external circumference, said base portion being provided with a first recess having a diameter for receiving the ball, the external circumference of said base portion being provided with at least a second recess to provide clearance for the lower portion of the prosthesis;

a plurality of cap screws provided in corresponding apertures in said base portion for causing a high compression interference between an upper portion of the ball of the prosthesis and an internal surface of said first recess, a face of each of said cap screws contacting a lower edge of the ball at a point below a midpoint of the diameter of the ball; and a connector for connecting said adaptor to the ultrasonic device, wherein said first recess has a first longitudinal axis extending through an external opening thereof, said connector has a second axis of propagation of ultrasonic energy, and said first axis extends within about 45° of normal to said second axis.

2. The adaptor of claim 1, wherein said cap screws are spaced an equal distance from one another around said external circumference of said base portion.

3. The adaptor of claim 1, wherein said base portion defines a third recess and a fourth recess to permit variable positioning of said base portion on the prosthesis while providing clearance for the lower portion of the prosthesis, said second, third, and fourth recesses being spaced an equal distance from one another around said external circumference of said base portion.

4. The adaptor of claim 1, wherein said connector comprises a bore supporting a plurality of threads.

5. An adapter for connecting an ultrasonic device to a prosthesis, the prosthesis of the type comprising a proximal body including a ball of a giving radius of curvature defining a generally spherical surface, said proximal body exposed outside of the bone, and a distal stem extending within the bone, said adapter comprising:

a body defining an external aperture which opens into an internal recess defined by an arcuate inner surface, said recess being sized to receive the prosthesis ball and having a longitudinal axis that extends through said external aperture, said inner surface having a radius of curvature substantially equal to that of the prosthesis ball so as to contact a portion of the surface of the prosthesis ball;

at least one engagement element being configured to engage a portion of the surface of the ball opposite of said body inner surface and being adapted to connect to said body to compress the ball against said inner surface; and a connector being configured to couple said body to the ultrasonic device, said connector having an axis of ultrasonic energy propagation which extends within about 65° of normal to said recess longitudinal axis.

6. The adapter of claim 5, wherein said engagement element comprises a cap screw provided in a corresponding aperture in said body.

7. The adapter of claim 5, wherein said adapter comprises a plurality of engagement elements spaced an equal distance from one another around an external circumference of said base.

8. A method for implanting an orthopedic prosthesis comprising the steps of:

ultrasonically vibrating an object with sufficient energy to disrupt cancellous bone, the object having substantially the same shape as a prosthesis to be implanted for forming a complementary cavity in cancellous bone, said object having a linear first axis extending between a first and second end thereof, and the ultrasonic energy being propagated from a source thereof to the object along a second axis which deviates from a perpendicular to the first axis by no more than about 45°; and implanting the prosthesis in the cavity.

9. A method as recited in claim 8 wherein the object comprises the prosthesis to be implanted, and further comprising:

discontinuing the ultrasonic vibrations; and leaving the prosthesis in the cavity so formed.

10. A method as recited in claim 9 comprising ultrasonically vibrating a prosthesis having a plurality of teeth on at least a portion of the surface of the prosthesis left in the cavity.

11. A method as recited in claim 10 wherein the teeth are spaced apart at a distance appropriate for ingrowth of cancellous bone.

12. A method as recited in claim 11 wherein the teeth are spaced apart at a distance in the range of from 50 to 400 micrometers.

13. A method of implanting an orthopedic prosthesis into a bone, said orthopedic prosthesis of the type having a proximal body which is exposed outside the bone, a distal stem which extends within the bone and a linear first axis which extends from a proximal end of said body to a distal end of said stem, said method comprising the steps of:

coupling an ultrasonic transducer to the proximal body of the prothesis;

propagating ultrasonic energy from said ultrasonic transducer to the prosthesis along a second axis which deviates from a perpendicular to said first axis by no more that about 65°; and driving the prosthesis into the bone.

14. The method of claim 13, wherein said step of driving the prosthesis into the bone comprises applying a driving force to the proximal body of the prosthesis in a direction generally parallel to said first axis.

15. The method of claim 13, wherein the ultrasonic energy is applied simultaneously with said driving force.

16. The method of claim 13, wherein said ultrasonic energy is insufficient for significantly disrupting cortical bone.

17. The method of claim 13, wherein said second axis deviates from a perpendicular to said first axis by no more than 45°.

18. The method of claim 13, wherein said second axis is generally perpendicular to said first axis.

19. A method of providing a canal in a bone to receive an orthopedic prosthesis, said method comprising the steps of:

coupling an ultrasonic transducer to an implantation tool having substantially the same shape as the prothesis, said implantation tool having a linear first axis extending between a distal end and a proximal end thereof;

propagating ultrasonic energy along a second axis which deviates from a perpendicular to said first axis of said implantation tool by no more than about 65°; and inserting said implantation tool into the bone.

20. The method of claim 19, wherein said second axis deviates from a perpendicular to said first axis by no more than about 45°.

21. The method of claim 20, wherein said second axis is generally perpendicular to said first axis.

22. The method of claim 19, wherein said step of coupling said ultrasonic transducer to said implantation tool comprises coupling a broach to said ultrasonic transducer.

23. The method of claim 22, wherein said broach comprises rasp-like teeth.

* * * * *

UNITED STATES PATENT AND TRADEMARK OFFICE
CERTIFICATE OF CORRECTION

PATENT NO. : 5,330,481
DATED : July 19, 1994
INVENTOR(S) : Larry L. Hood et al

It is certified that error appears in the above-indentified patent and that said Letters Patent is hereby corrected as shown below:

Column 4, line 4, change "Figure 3B" to --Figures 3D-3F--

Column 6, line 7, change "Figure 3A" to --Figures 3A-3C--

Column 6, line 28, change "Figure 3B" to --Figures 3D-3F--

Figure 3G:
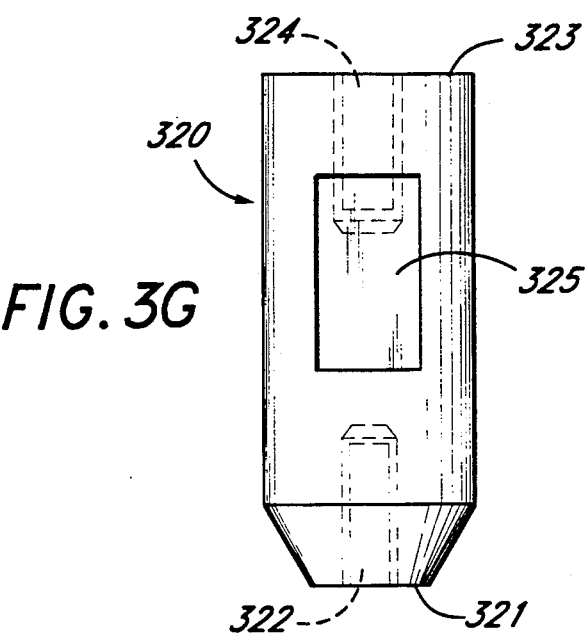
Figure 3I:
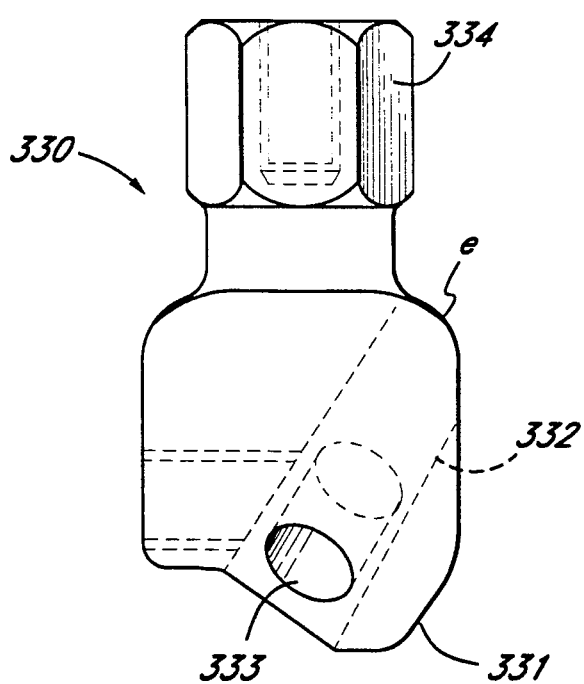
Figure 3H:
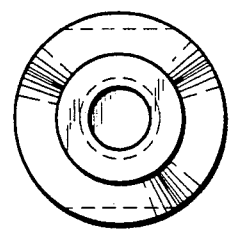

Column 6, line 40, change "Figure 3C" to --Figures 3G-3H--

Figure 3J:
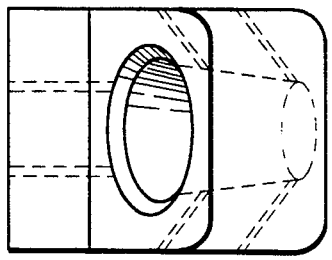

Column 6, line 57, change "Figure 3D" to --Figures 3I-3J--

Figure 3K:
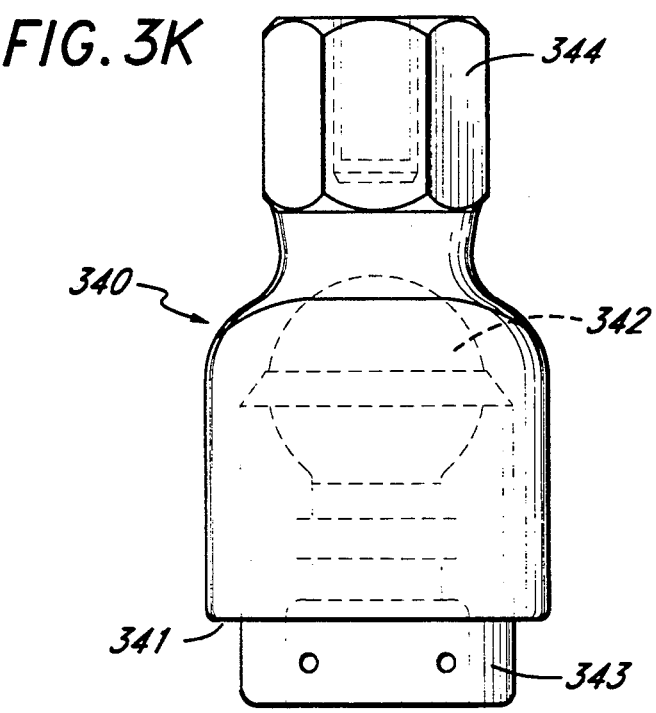
Figure 3L:
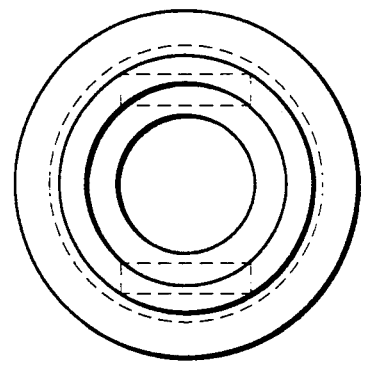

Column 7, line 12, change "Figure 3E" to --Figures 3K-3L--

Column 8, line 11, change "8" to --θ--

Column 10, line 19, change "Figure 3B" to --Figures 3D-3F--

Signed and Sealed this

Seventeenth Day of October, 1995

Attest:

BRUCE LEHMAN

Attesting Officer

Commissioner of Patents and Trademarks